United States Patent
Ackermann et al.

(10) Patent No.: US 11,370,071 B2
(45) Date of Patent: Jun. 28, 2022

(54) JOINING METHOD FOR A MEDICAL DEVICE

(71) Applicant: Aesculap AG, Tuttlingen (DE)

(72) Inventors: Janina Ackermann, Tuttlingen (DE); Sven Barthelmes, Emmingen-Liptingen (DE); Jan Dahmen, Seitingen-Oberflacht (DE); Andreas Deutschendorf, Spaichingen (DE); Till Mattes, Neuhausen ob Eck (DE); Elke Pleil, Bad Dürrheim (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 17/420,220

(22) PCT Filed: Jan. 2, 2020

(86) PCT No.: PCT/EP2020/050037
§ 371 (c)(1),
(2) Date: Jul. 1, 2021

(87) PCT Pub. No.: WO2020/141197
PCT Pub. Date: Jul. 9, 2020

(65) Prior Publication Data
US 2022/0063026 A1    Mar. 3, 2022

(30) Foreign Application Priority Data
Jan. 2, 2019    (DE) .................... 10 2019 100 016.5

(51) Int. Cl.
*B23P 11/02* (2006.01)
*A61B 17/56* (2006.01)
*A61B 17/00* (2006.01)

(52) U.S. Cl.
CPC ............ *B23P 11/025* (2013.01); *A61B 17/56* (2013.01); *A61B 2017/00477* (2013.01); *A61B 2017/00526* (2013.01); *A61B 2017/00836* (2013.01)

(58) Field of Classification Search
CPC ........ B23P 11/025; A61B 17/56; A61B 17/88; A61B 17/92; A61B 2017/00526;
(Continued)

(56) References Cited

U.S. PATENT DOCUMENTS 7,736,377 B1 * 6/2010 Anson ............ A61B 17/320725
606/153
8,579,985 B2 * 11/2013 Podolsky ................ A61F 2/367
623/22.42
(Continued)

FOREIGN PATENT DOCUMENTS

DE    10322156 A1 * 11/2003 .............. H01J 35/26
DE    10322156 A1    11/2003
(Continued)

OTHER PUBLICATIONS

Written Opinion received in International Application No. PCT/EP2020/050037 dated Apr. 23, 2020, with translation, 14 pages.
(Continued)

*Primary Examiner* — Bayan Salone
(74) *Attorney, Agent, or Firm* — Culhane Meadows, PLLC; Christopher A. Rothe

(57) ABSTRACT

A joining method for a medical device, in particular a surgical instrument or implant, with a shaft and an attachment to be secured on the shaft, the method having the following steps: heating the attachment or cooling the shaft, such that an internal diameter of an opening of the heated attachment is greater than an external diameter of the shaft, then placing the shaft into the opening of the attachment, and
(Continued)

then cooling the attachment, so as to shrink the attachment onto the shaft in a manner substantially free of gaps, or heating the shaft, such that the shaft and the opening are connected by an interference fit. A corresponding medical device is produced by the joining method.

13 Claims, 2 Drawing Sheets

(58) Field of Classification Search
CPC ........... A61B 2017/00477; A61B 2017/00836; A61B 2090/0813
See application file for complete search history.

(56) References Cited

U.S. PATENT DOCUMENTS

| | | | |
|---|---|---|---|
| 8,897,420 B1* | 11/2014 | Hunt | H01J 35/1024 378/132 |
| 2003/0157459 A1* | 8/2003 | Augthun | A61C 8/0069 433/173 |
| 2003/0215059 A1* | 11/2003 | Higgins | H01J 35/26 378/132 |
| 2004/0117024 A1* | 6/2004 | Gerbec | A61F 2/38 623/20.15 |
| 2006/0206210 A1* | 9/2006 | Abicht | A61F 2/389 623/18.11 |
| 2012/0130502 A1 | 5/2012 | Podolsky et al. | |

FOREIGN PATENT DOCUMENTS

| | | | | |
|---|---|---|---|---|
| DE | 69927035 T2 * | 6/2006 | | A61B 17/064 |
| DE | 69927035 T2 | 6/2006 | | |
| DE | 102013101231 A1 * | 8/2013 | | H01J 35/101 |
| DE | 102013101231 A1 | 8/2013 | | |
| DE | 202013012364 U1 | 6/2016 | | |
| DE | 202013012364 U1 * | 8/2016 | | A47K 3/40 |
| EP | 2669032 A1 * | 12/2013 | | B23B 31/005 |
| EP | 2669032 A1 | 12/2013 | | |
| WO | 0180768 A1 | 11/2001 | | |
| WO | WO-0180768 A1 * | 11/2001 | | A61C 8/005 |
| WO | 2004052244 A1 | 6/2004 | | |
| WO | WO-2004052244 A1 * | 6/2004 | | A61F 2/389 |

OTHER PUBLICATIONS

Search Report received in German Application No. 10 2019 100 016.5 dated Aug. 20, 2019, with translation, 14 pages.
Search Report received in International Application No. PCT/EP2020/050037 dated Apr. 23, 2020, with translation, 6 pages.

* cited by examiner

JOINING METHOD FOR A MEDICAL DEVICE

CROSS-REFERENCE TO RELATED APPLICATIONS

This application is the United States national phase entry of International Application No. PCT/EP2020/050037, filed Jan. 2, 2020, and claims the benefit of priority of German Application No. 10 2019 100 016.5, filed Jan. 2, 2019. The contents of International Application No. PCT/EP2020/050037 and German Application No. 10 2019 100 016.5 are incorporated by reference herein in their entireties.

FIELD

Medical devices are subject to high requirements with regard to functional safety, tolerances and in particular sterility/maintaining sterility. This applies in particular to connection points of devices where two components are firmly joined together. The following is an example of the connection point of a surgical instrument with a handhold and an operating end, for example a surgical hammer. However, it should be noted that the same problem is applicable to a variety of other medical devices and various connection points thereof.

BACKGROUND

According to the current prior art, handholds and operating ends (effectors) are joined by pressing them together, for example by hand, and by securing them against axial and radial slippage via a transverse pin or locking pin. The transverse pin is pressed into a bore which runs through the handhold and the operating end and then has to be fitted by grinding, and the surface has to be brushed off. These processes are costly and time-consuming. Furthermore, gaps are created or remain in such compression connections, into which deposits form and blood, germs, dirt and chemical processing agents etc. diffuse, which cannot be removed during cleaning. This adversely leads to contamination and corrosion of the connection point. In order to avoid this, the connection point may be subsequently shielded by welding or bonding, which further complicates the manufacturing process and makes it more expensive. Other joining methods, according to which two components of a medical device are joined together under thermal load/influence, have been essentially neglected in the past, since thermal distortion outside the prescribed tolerances of at least one of the components to be joined was basically expected.

SUMMARY

The invention is based on an object to reduce or avoid disadvantages of the prior art and to provide a cost-effective joining method for a stable, non-losable connection of two components of a medical device, which meets the high requirements for sterility.

This object is solved by a joining method, a medical device (e.g. medical/surgical instrument) and the use of a corresponding joining method for manufacturing a medical device (e.g. medical/surgical instrument).

The core of the present invention therefore consists in connecting two components of a medical device, in particular of a medical (surgical) instrument, which are to be joined together by thermal shrink-fitting. In accordance with the invention, care should be taken to ensure that preferably only the component which is subject to lower requirements as compared to the other component, for example with regard to dimensional tolerances and/or material properties, is essentially thermally processed. Alternatively or additionally, only the component that has a greater heat capacity as compared to the other component (e.g. as a result of greater mass) should preferably be essentially thermally processed. Alternatively or additionally, only the component should preferably be essentially thermally processed which, due to its structure and/or its spatial dimensions/shape, shows lower distortion tendencies as a result of heat input as compared to the other component. Alternatively or additionally, only the component should be essentially thermally processed which consists of a material that has thermal advantages over the material of the other component, for example which deforms sufficiently at a lower temperature as compared to the other component in order to enable a shrinking process.

For example, a generic medical device (medical instrument) may consist of, among other things, an (elongated/slim) instrument shaft and an instrument handhold connected/to be connected thereto and/or an effector connected/to be connected thereto (e.g. hammer head, claw, etc.). In such an example, according to the invention, the effector with a more robust design (shorter, thicker, more solid, etc.) than the instrument shaft would be the component which exhibits a lower thermally induced distortion tendency than the instrument shaft and is thus (exclusively) subjected to thermal treatment for subsequent shrink-fitting.

The object underlying the invention is solved in particular by a joining method for a medical device, in particular a surgical instrument or implant, having a shaft made, for example, of titanium and an attachment (handhold, effector, etc.) to be fastened thereon, for example made of steel, wherein the joining method comprises the following steps:

First, the attachment is heated or the shaft is cooled so that it expands or shrinks due to thermal expansion or shrinkage in accordance with the material-specific expansion coefficient, whereby the inner diameter of a (receiving) opening of the attachment is/becomes larger than an outer diameter of the shaft (to be inserted).

Subsequently, the shaft is inserted into the opening of the attachment. That is, due to the thermal expansion of the attachment or the thermal shrinkage of the shaft, the opening is/becomes enlarged relative to the shaft cross-section, and the shaft and the attachment are freely movable relative to each other in this state in the axial direction of the shaft.

Subsequently, i.e. after insertion of the shaft into the corresponding attachment opening, the attachment is cooled (actively or passively) in order to shrink it onto the shaft essentially without a gap, or the shaft is heated (actively or passively) in order to expand it within the attachment so that the shaft and the opening form an interference fit or press fit (i.e. a compression connection), preferably at the maximum ambient temperature to be expected in operation, further preferably at room temperature.

This joining method, which is used for the first time in medical devices, is at least partially or even fully automatable and requires no or only a few, less demanding, manual steps (one process step) on the part of the user. That is, manual labor is reduced and some cost-intensive, manual operations as well as the transverse pin are no longer required during assembly. Thus, a simple, fast and cost-effective as well as validatable and non-losable connection of two components of the medical device is made possible, which also meets the strict requirements for sterility/cleanability. In addition, the external appearance, quality and load capacity of the connection and the device are also improved, so that higher (holding and/or torsional) forces can be transmitted than with previous solutions. In addition, repetition accuracy/reproducibility and process reliability of the joining method are improved. Accordingly, the process is suitable for serving as a basis for standardizing various medical technology connection points or interfaces, thereby reducing the costs of overall production. It is also particularly important that this method, due to high contact force within the interference fit, ensures that a gap between the shaft and the attachment is essentially completely closed during cooling and that verifiably no contamination and corrosion takes place within the connection point during the intended operation of the medical device, in particular when used in a surgical environment and subsequent chemical/thermal (sterilization) reprocessing.

The shaft may have an undercut-free, round or polygonal, for example, quadrangular or hexagonal cross-section. Furthermore, the attachment may be tapered on a side at which the shaft protrudes from the attachment mounted thereon (in the case of a surgical instrument, at a proximal end), such that an angle greater than 90° is formed at a transition point between the shaft and the attachment, making the transition point more accessible for cleaning and sterilization and/or making the transition point less susceptible to the formation of deposits. Furthermore, it should be noted that the shaft and the attachment may be made of different materials. In the preceding example, according to which the shaft is made of titanium and the attachment is made of steel, both components can be heated together if applicable, since steel has a higher thermal expansion or respectively a higher coefficient of linear expansion and thus the necessary expansion of the opening of the attachment can also be achieved during joint heating without the (titanium) shaft exhibiting undue distortion tendencies.

It should be noted that due to the special requirements and materials of medical products, in particular the geometric design of such a connection point and the selection of the usable temperature range are important aspects which will be discussed in more detail below.

According to one aspect, parameters are freely programmable or adjustable for a control, preferably a feedback control, for controlling or feedback controlling the joining method in order to enable adaptation of the joining method to deviating ambient conditions or for joining different devices with different dimensions and/or materials. Adjustable parameters here are, for example, the heating or cooling power, the heating or cooling time and the heating or cooling power curve. Thus, the method according to the invention can be applied to a single machine or station for carrying out this method for the production of different medical devices.

Preferably, during the joining method there is furthermore a monitoring of the temperature of the attachment and/or of the shaft and further preferably of the heating and/or cooling time. For this purpose, for example, at least one pyrometer can be used as a temperature sensor. This ensures that the shaft can be easily inserted into the opening at the right time and that the joining method is not terminated too early, which could cause the attachment and the shaft to slip or even separate. In addition, it can be prevented that the attachment or, if applicable, also the shaft are heated or cooled too much during contact with the attachment, so that no disadvantages are generated with regard to the mechanical properties of the corresponding components during or after heating or cooling. The pyrometer can be oriented correctly by hand or automatically, e.g. using markers, immediately before the start of the measurement and/or during the measurement. Alternatively, contact thermometers or the like can be attached instead of one or more pyrometers, for example.

In particular, it is advantageous if the temperature of the attachment or the shaft is monitored at at least two points (positions): close to, preferably directly at the opening (i.e. at its inner circumferential surface or directly next to or at an edge at an opening exit) or at the outer circumference of one end of the shaft to be inserted into the attachment as well as at an attachment border region spaced therefrom (i.e. as far away as possible from the opening) or at a shaft region spaced therefrom. This makes it possible to monitor and compare the temperatures at different relevant points when adjusting process parameters, and thus also to monitor the heat conduction within the attachment or the shaft during heating and, if applicable, cooling, in order to set or control an optimum process sequence.

A temperature measurement on the shaft (e.g. at a stationary point or a point that can be moved during the joining method) is advantageous, for example, when cooling it down. Alternatively or additionally, this is advantageous in order to determine or specify a required minimum temperature of the attachment in relation to the shaft temperature or room temperature, which may correspond to each other (in particular if the shaft is not heated or cooled), and/or a minimum temperature difference between the attachment and/or the shaft and/or the room temperature. Furthermore, it is advantageous if temperature monitoring is carried out in the axial course of the opening and/or the shaft, in particular the shaft tip (of a shaft section which is received in the opening), in order to avoid or reduce axial stresses after cooling. In other words, a (spatially resolved and/or time-resolved) temperature profile is determined preferably axially along the shaft and/or the shaft tip (along its axial extension/axial course) and/or axially along an inner circumferential surface of the opening (along the axial course inside the opening), for which purpose, for example, two or more points for temperature measurement and/or measuring points can be provided distributed in the axial direction on the shaft and/or inside the opening.

Preferably, induction heating is used for heating the attachment or nitrogen is used for cooling the shaft. In particular, heating by induction heat is a simple, safe, fast-acting and easily controllable heating method in which open heat sources are avoided, thereby reducing the risk of injury. Alternatively, a heating plate or resistance heater or the like may be used.

According to one aspect of the invention, the joining method may further include adjusting a heat input during heating depending on component parameters of the attachment and, if applicable, of the shaft. For example, the geometry, the surface condition, the dimensioning, the heat treatment condition, the expansion coefficients and/or the corrosion resistance of the attachment and/or of the shaft can be taken into account as component parameters. In particular, the consideration of the expansion coefficient and the heat treatment condition, i.e. properties of materials specifically used in medical technology, is important in order not to negatively influence the corrosion resistance.

The interference fit of the shaft and of the attachment is preferably dimensioned in such a way that the shaft and the attachment are axially and radially inseparably (non-losably) connected to each other during operation. This is important in order to ensure the functional reliability of the device. It is taken into account that the shaft and the attachment may be made of different materials with different coefficients of thermal expansion and that the interference fit is designed in such a way that the compression connection is ensured at least in a temperature range intended for operation of the device. Further preferably, the corresponding connection is reversibly releasable by reheating, for example in order to enable quick and easy repair or replacement of the shaft and/or of the attachment in a service case. It has proven useful if the interference fit has an allowance for interference of between 20 and 55 µm. Depending on the application of the medical device, different requirements can be placed on the strength of the connection and the allowance for interference can therefore be designed differently. For example, in a first, low-load application, a smaller allowance for interference, for example from 20 to 25 µm, in a second, medium-load application, a medium allowance for interference, for example from 35 to 40 µm, or in a third, high-load application, a large allowance for interference, for example from 50 to 55 µm, can be provided. That is, the geometrical design of the shaft and of the attachment, in particular of the opening of the attachment, depends on the application of the product.

Preferably, the heating temperature of the attachment is between 50 and 350° C., preferably between 300 and 350° C. This allows sufficient expansion of the opening without adverse effects on the mechanical properties of the shaft or the attachment.

According to another aspect of the invention, the insertion of the shaft into the opening of the attachment can be performed via a linear unit. This makes it possible to automate or at least simplify, in addition to the heating and cooling, the insertion of the shaft into the opening of the attachment, thus further reducing manufacturing costs. Furthermore, an insertion depth of the shaft is precisely controllable and reproducible and handling by the user is further reduced, thus reducing both the risk of injury to the user on the hot attachment as well as human errors. The linear unit can take over the attachment already at the heating or cooling unit or hold it already during heating or cooling. When the attachment is removed from the heating or cooling unit after heating or cooling or is moved to be placed on the shaft, the heating or cooling unit is already ready to heat the next attachment and the production cycle can be increased. In this case, the linear unit is of particular advantage, since the insertion of the shaft into the attachment may have to be carried out very precisely and very quickly in view of the sometimes high degree of miniaturization of the medical devices, since the dimensions and tolerances are very small and the components cool down or heat up quickly. If this were done manually by a user, the potential for error would likely be high. Alternatively, the linear unit can hold the shaft and insert it/place it into the opening of the positionally-fixed attachment. In this case, the attachment or the shaft does not have to be moved at all in the heated or cooled state and it is sufficient to switch off the heating or cooling unit to initiate cooling or heating of the attachment or the shaft.

Furthermore, the object underlying the invention is solved by a medical device, in particular a surgical instrument or implant, which has an attachment with an opening and a shaft inserted into the opening, wherein an outer diameter of the shaft and an inner diameter of the opening of the (cooled) attachment are dimensioned to form an interference fit or crimp connection, and the attachment is connected to the shaft by the aforementioned joining method. Preferably, the shaft is a handle or handhold and the attachment is an operating end or tool head of a medical instrument. With regard to advantages and further details of this device, reference is made to the preceding description of the associated joining method.

Furthermore, the object is solved by using the preceding joining method for manufacturing a medical device, in particular a medical instrument or implant, preferably according to the preceding description, which comprises an attachment and a shaft inserted into an opening of the attachment. With regard to advantages and embodiments of the joining method and of the medical device, reference is made to the preceding description.

BRIEF DESCRIPTION OF THE DRAWING FIGURES

DETAILED DESCRIPTION

Figure 1A:
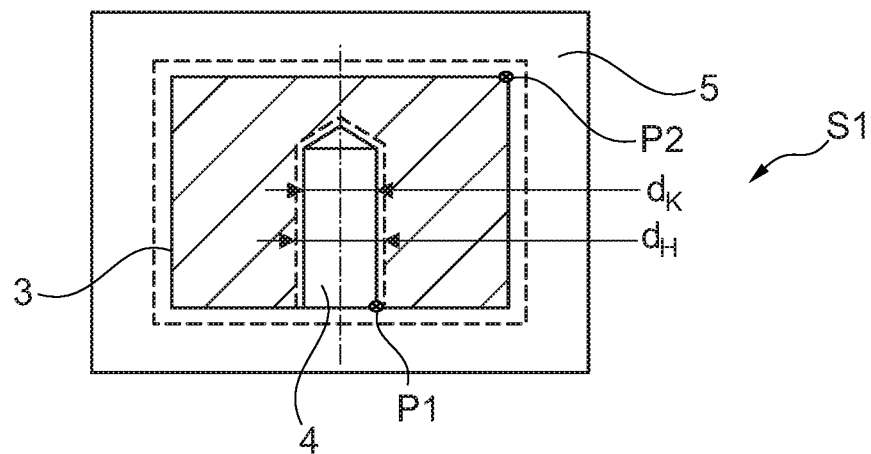
FIGS. 1A, 1B and 1C show successive steps of a joining method according to the invention in accordance with an embodiment, shown in schematic representation.
Figure 1B:
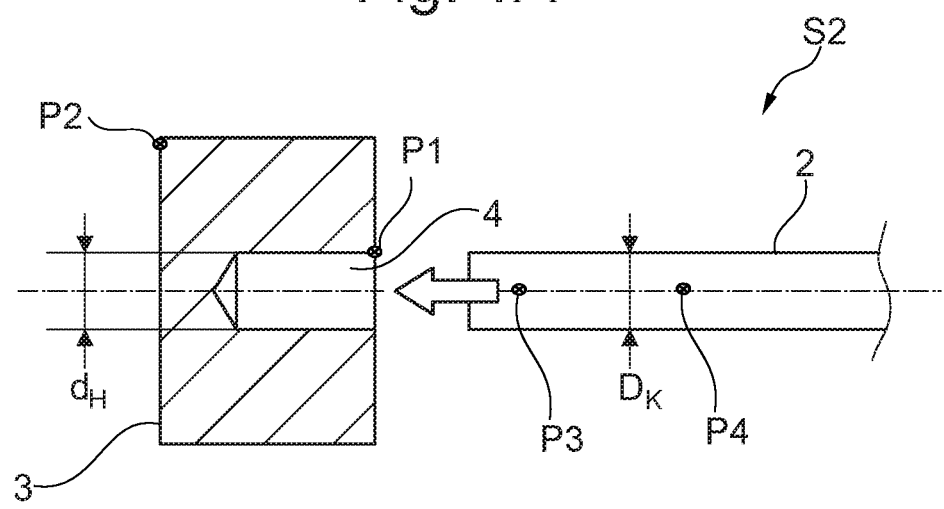
Figure 1C:
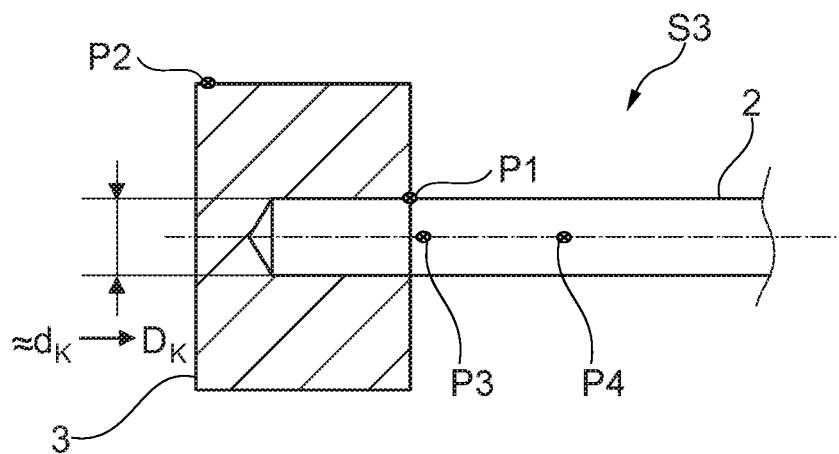

FIGS. 1A, 1B and 1C show an embodiment of a joining method according to the invention for a medical device 1, which for illustration purposes is shown here as a surgical instrument with a shaft or handle 2 and a simple, cylindrical or cuboid attachment or operating end 3, e.g. in the manner of a surgical hammer. However, depending on the application, any other differently shaped operating ends 3 can be selected.

FIG. 1A illustrates the step of heating S1. An operating end 3, which has an opening 4, in this example a bore or a blind hole, is arranged on an induction heating 5 and is heated by induction heat. Preferably, a temperature (possibly a temporal and/or local (axial) temperature profile) of the attachment or of the operating end 3 is measured at a point P1 close to an edge of the opening and/or at a point P2 of the attachment spaced apart therefrom. Alternatively or additionally, a temperature of the shaft or handle 2 is optionally measured at a point P3 close to a handle end/shaft end to be inserted into the opening 4 and at a point P4 at a further handle region/shaft region spaced apart therefrom. Due to the thermal expansion of a material of the operating end 3, the operating end 3 expands, which also enlarges the opening 4. That is, the opening 4 has a first 'cold' inner diameter $d_K$ at room temperature and has a second, 'hot' inner diameter $d_H$ in the heated state, which is larger than the cold inner diameter $d_K$.

After the operating end 3 has been heated to a certain temperature and/or during a certain heating time (wherein the temperature can be measured, for example, at the point P1 and/or P2), the handle 2, whose 'cold' outer diameter D (i.e., preferably at room temperature or maximum ambient temperature to be expected during operation, wherein the handle temperature or shaft temperature can be measured/monitored e.g. at the point P3 and/or P4 on the handle 2) has a certain allowance for interference with respect to the cold inner diameter $d_K$ of the operating end 3, but is smaller than the hot inner diameter $d_H$ present at this point in time, is inserted (S2) into the opening 4 in the longitudinal direction of the handle 2.

Subsequently, the operating end 3 cools down (S3), whereby the opening 4 also shrinks/narrows and the operating end 3 shrinks onto the handle 2. That is, as shown in FIG. 1C, a crimp connection of the handle 2 with the operating end 3 is established due to an interference fit/press fit. Preferably, the temperature of the shaft/handle 2 and/or of the operating end 3 is correspondingly measured at points P1 and/or P2 and/or P3 and/or P4. Due to the allowance for interference of the handle 2 at room temperature, an inner circumferential surface of the opening 4 is axially and radially immovable (with respect to forces occurring during an intended use) and pressed against an outer circumferential surface of the handle 2.

Figure 2:
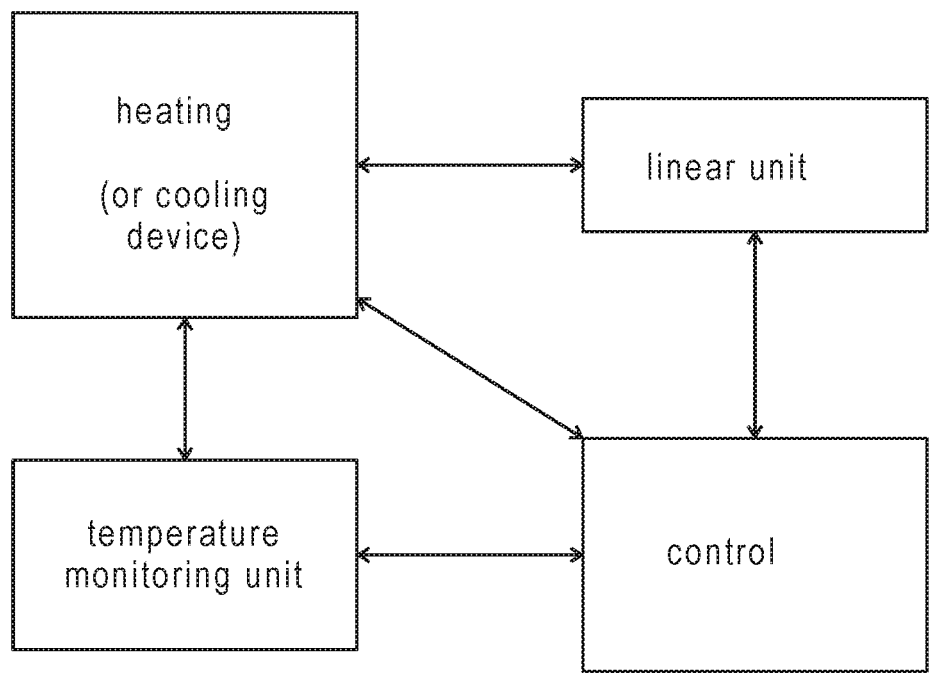
FIG. 2 shows an example of a manufacturing arrangement for the joining method.

FIG. 2 shows an exemplary manufacturing arrangement for the aforementioned joining method. A heating 5, in this example an induction coil, is provided, which is used in step S1 for heating the operating end 3. A temperature monitoring unit 6 detects, for example via a pyrometer, a temperature of the operating end 3 at several points (step S4) and determines a temperature deviation and, if applicable, a heat input. A control unit 7, which monitors the heating time and specifies a target temperature and, if applicable, a temperature profile or heat input, receives monitoring signals from the temperature monitoring unit and controls the heating 5 on the basis of these signals (step S5).

If a target temperature is reached, a signal, e.g. a sound or light signal, is output and the operating end 3 is transferred by a user to a linear unit 8 or the operating end 3 is taken over fully automatically by the linear unit 8. The linear unit 8 is used to push/place the operating end 3 securely and evenly onto the handle 2 in step S2 so that it is correctly positioned in the handle 2 after cooling (S3) of the operating end 3. Alternatively, placing the operating end 3 can also be performed manually by the user. If placing or transferring of the operating end 3 to the linear unit 8 is performed by the user, the control unit 7 can also be configured to control the heating 5 in such a way that the operating end 3 is kept at the target temperature for a certain time. Subsequently, during cooling, the control unit 7 can monitor the cooling time and, via the temperature monitoring unit 6, the temperature of the operating end 3 in order to determine when the operating end 3 and the handle 2 are sufficiently tight on each other and, if applicable, can be handled without risk of injury to a user. At this point, another signal may be output.

Figure 3:
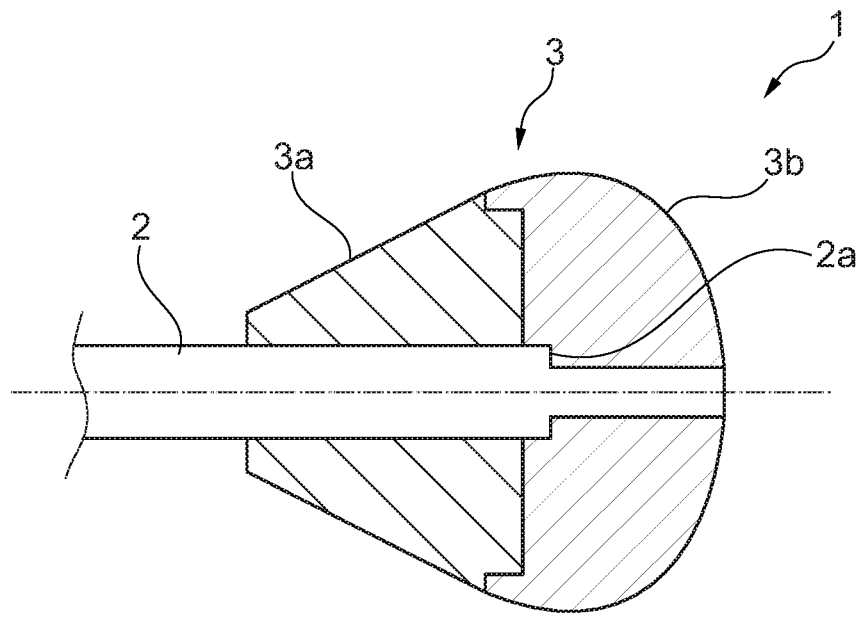
FIG. 3 shows an example of another embodiment of the attachment.

FIG. 3 shows an example of another embodiment of the attachment or operating end 3. Here, several aspects to be considered independently of each other are shown, which can be implemented in any combination or individually in an operating end 3 according to the invention. A first aspect relates to a substantially teardrop-shaped cross-section of the operating end 3, wherein the tip of the teardrop points towards the shaft or handle 2. In other words, the cross-section of the operating end 3 tapers towards the shaft or handle 2 (where it protrudes proximally from the operating end). This improves accessibility of the edge at the transition between the operating end 3 and the handle 2 for cleaning and/or sterilization purposes.

A second aspect relates to an operating end 3 that has multiple parts. In this regard, a first, proximal attachment part 3a (i.e., located closer to a proximal handle end to be handled) is shrunk or shrinkable to the handle 2, and a second, distal attachment part 3b may be formed, for example, as a disposable part and be attachable to the instrument (i.e., to the proximal attachment part 3a already connected to the handle 2). Alternatively, the distal attachment part 3b may first be connected to the proximal attachment part 3a and then be shrunk onto the handle 2 together with the latter, wherein the provided interfaces and diameters have to be precisely matched to each other in order not to damage each other during thermal expansion and subsequent shrinking. The distal attachment part may be distally closed or open in the longitudinal direction of the handle 2.

A third aspect relates to defining the position of the handle 2 with respect to the operating end 3 in the longitudinal direction of the handle 2. The handle 2 may form a step or shoulder 2a that is provided to abut on a complementary shoulder or step of the operating end 3 in the longitudinal direction.

A fourth aspect relates to a formation of the opening 4 of the attachment 3 as a through hole. This can prevent air from being trapped in a pocket between an opening wall and the distal end of the handle 2, which could affect correct positioning in the axial direction. In this case, it is advantageous if the handle 2 is positioned in the attachment 3 in the longitudinal direction of the handle 2 in such a way that a distal handle end is flush with the attachment 3 to avoid an additional edge, which would have to be cleaned.

It should be noted that the aforementioned embodiment can also be adapted in such a way that instead of heating, a cooling device can also be provided and instead of heating the attachment, cooling of the shaft by this cooling device can also be provided, wherein the shaft is heated after insertion of the shaft into the opening of the attachment in order to establish the press fit.

The invention claimed is:

1. A joining method for a medical device which is a surgical instrument or implant having a shaft and an attachment to be fixed thereto, the method comprising the steps of:
   heating the attachment or cooling the shaft so that an inner diameter of an opening of the attachment is larger than an outer diameter of the shaft,
   subsequently inserting the shaft into the opening of the attachment,
   subsequently cooling the attachment in order to shrink it onto the shaft substantially without a gap, or heating the shaft in order to expand it within the opening of the attachment, so that the shaft and the opening are connected via an interference fit, and
   monitoring a temperature of the attachment or respectively of the shaft at at least a first point close to the opening or respectively at an outer circumference of an end of the shaft to be inserted into the attachment as well as at a second point at an attachment border region or respectively shaft region spaced apart from the first point.

2. The joining method according to claim 1, further comprising the step of monitoring the temperature of the attachment.

3. The joining method according to claim 2, wherein the temperature of the attachment is monitored on the opening as well as at an attachment border region spaced apart therefrom.

4. The joining method according to claim 1, wherein an induction heating is used for heating the attachment.

5. The joining method according to claim 1, further comprising the step of adjusting a heat input during heating depending on parameters of the shaft and of the attachment.

6. The joining method according to claim 1, wherein the interference fit is dimensioned in such a way that the shaft and the attachment are axially and radially connected to each other in an inseparable manner during operation.

7. The joining method according to claim 1, wherein the interference fit has an allowance for interference between 20 and 55 µm.

8. The joining method according to claim 1, wherein the shaft is made of titanium and the attachment is made of steel.

9. The joining method according to claim 1, wherein a maximum heating temperature of the attachment is between 50 and 350° C.

10. The joining method according to claim 1, wherein insertion of the shaft into the opening of the attachment takes place via a linear unit.

11. A medical device comprising:
an attachment with an opening; and
a shaft inserted in the opening,
wherein an outer diameter of the shaft and an inner diameter of the opening are dimensioned to form an interference fit, and
wherein the attachment is connected to the shaft by the joining method according to claim 1.

12. The medical device according to claim 11, wherein the shaft is a handle or handhold and/or the attachment is an operating end or tool head.

13. The medical device according to claim 11, wherein the shaft is made of titanium and/or the attachment is made of steel.

* * * * *